(12) United States Patent
Gladwin et al.

(10) Patent No.: US 11,986,493 B2
(45) Date of Patent: *May 21, 2024

(54) INORGANIC NITRITE TO IMPROVE CARDIOPULMONARY HEMODYNAMICS

(71) Applicant: University of Pittsburgh—Of the Commonwealth System of Higher Education, Pittsburgh, PA (US)

(72) Inventors: Mark Thomas Gladwin, Pittsburgh, PA (US); Edwin Parsley, Houston, TX (US); Hunter Clay Champion, Midland, GA (US)

(73) Assignees: University of Pittsburgh—Of the Commonwealth System of Higher Education, Pittsburgh, PA (US); Aires Pharmaceuticals, Inc., San Diego, CA (US)

( * ) Notice: Subject to any disclaimer, the term of this patent is extended or adjusted under 35 U.S.C. 154(b) by 52 days.

This patent is subject to a terminal disclaimer.

(21) Appl. No.: 17/540,965

(22) Filed: Dec. 2, 2021

(65) Prior Publication Data

US 2022/0088065 A1 Mar. 24, 2022

Related U.S. Application Data

(63) Continuation of application No. 15/954,304, filed on Apr. 16, 2018, now Pat. No. 11,219,640, which is a continuation of application No. 14/768,198, filed as application No. PCT/US2014/019703 on Feb. 28, 2014, now abandoned.

(60) Provisional application No. 61/771,063, filed on Feb. 28, 2013.

(51) Int. Cl.
*A61K 33/00* (2006.01)
*A61K 9/00* (2006.01)
*A61K 31/04* (2006.01)

(52) U.S. Cl.
CPC .............. *A61K 33/00* (2013.01); *A61K 9/007* (2013.01); *A61K 9/0073* (2013.01); *A61K 31/04* (2013.01)

(58) Field of Classification Search
CPC ...... A61K 33/00; A61K 9/007; A61K 9/0073; A61K 31/04; A61P 9/04; A61P 9/12
See application file for complete search history.

(56) References Cited

U.S. PATENT DOCUMENTS

| | | | |
|---|---|---|---|
| 4,889,116 A | 12/1989 | Taube | |
| 5,427,797 A | 6/1995 | Frostell et al. | |
| 5,873,359 A | 2/1999 | Zapol et al. | |
| 2007/0154569 A1 | 7/2007 | Gladwin et al. | |
| 2010/0092441 A1 | 4/2010 | Lundberg et al. | |
| 2010/0247681 A1 | 9/2010 | Gladwin et al. | |
| 2010/0247682 A1 | 9/2010 | Gladwin et al. | |
| 2012/0195983 A1 | 8/2012 | Gladwin et al. | |
| 2012/0208762 A1 | 8/2012 | Dudley | |

FOREIGN PATENT DOCUMENTS

| | | |
|---|---|---|
| EP | 0089070 A2 | 9/1983 |
| JP | 2007528855 A | 10/2007 |
| JP | 2010519335 A | 6/2010 |
| JP | 2016507570 B2 | 3/2016 |
| WO | 0234303 A1 | 5/2002 |
| WO | 2005004884 A2 | 1/2005 |
| WO | 2008105730 A1 | 9/2008 |
| WO | 2012076667 A1 | 6/2012 |
| WO | 2012142413 A2 | 10/2012 |
| WO | 2013116194 A2 | 8/2013 |
| WO | 2014124256 A1 | 8/2014 |

OTHER PUBLICATIONS

Kitzman et al., "Exercising Intolerance in Patients with Heart Failure and Preserved Left Ventricular Systolic Function: Failure of the Frank-Starling Mechanism," J Am Coll Cardiol., 1991, pp. 1065-1072, vol. 17, No. 5.
Kitzman et al., "Pathophysiological Characterization of Isolated Diastolic Heart Failure in Comparison to Systolic Heart Failure," JAMA, 2002, pp. 2144-2150, vol. 288, No. 17.
Lam et al., "Pulmonary Hypertension in Heart Failure with Preserved Ejection Fraction," J Am Coll Cardiol., 2009, vol. 53, No. 13, pp. 1119-1126.
Larsen et al., "Dietary Inorganic Nitrate Improves Mitochondrial Efficiency in Humans," Cell Metab., 2011, pp. 149-159, vol. 13, No. 2.
Larsen et al., "Regulation of mitrochondrial function and energetics by reactive nitrogen oxides," Free Radical Biology and Medicine, 2012, pp. 1919-1928, vol. 53.
Latson et al., "Effect of Nitroglycerin on Aortic Impedance, Diameter, and Pulse-Wave Velocity," Circ Res., 1988, pp. 884-890, vol. 62, No. 5.
Lee et al., "Aging and Arterial Stiffness," Circ J., 2010, pp. 2257-2262, vol. 74, No. 11.
Lewis et al., "Characterization of health-related quality of life in heart failure patients with preserved versus low ejection fraction in CHARM," Eur J Heart Fail., 2007, pp. 83-91, vol. 9, No. 1.
Lundberg et al., "Roles of dietary inorganic nitrate in cardiovascular health and disease," Cardiovasc Res., 2011, pp. 525-532, vol. 89, No. 3.

(Continued)

*Primary Examiner* — David Browe
(74) *Attorney, Agent, or Firm* — The Webb Law Firm

(57) ABSTRACT

Disclosed herein are methods for treating acute or chronic heart failure using inorganic nitrite, such as sodium nitrite. The method includes administering to a subject in need of treatment a therapeutically effective amount of inorganic nitrite. The nitrite may be administered by inhalation and may be nebulized. The nitrite may be administered at an emitted dose or in an escalated titrated dose. The nitrite may be a liquid formulation or a dry powder formulation.

16 Claims, 5 Drawing Sheets

(56) References Cited

OTHER PUBLICATIONS

Lundberg et al., "The nitrate-nitrite-nitric oxide pathway in physiology and therapeutics," Nat Rev Drug Discov., 2008, pp. 156-167, vol. 7, No. 2.
Maeder et al., "Hemodynamic Basis of Exercise Limitation in Patients With Heart Failure and Normal Ejection Fraction," J Am Coll Cardiol., 2010, pp. 855-863, vol. 56, No. 11.
Maher et al., "Hypoxic Modulation of Exogenous Nitrite-Induced Vasodilation in Humans," Circulation, 2008, pp. 670-677, vol. 117, No. 5.
Maher et al., "Intra-Arterial Inorganic Nitrite Preferentially Dilates the Capacitance Bed in Chronic Heart Failure," Heart, 2009, p. 113, vol. 95, No. Suppl 1.
Massie et al., "Irbesartan in Patients with Heart Failure and Preserved Ejection Fraction," N Engl J Med., 2008, pp. 2456-2467, vol. 359, No. 23.
Mohammed et al., "Comorbidity and Ventricular and Vascular Structure and Function in Heart Failure with Preserved Ejection Fraction: A Community-Based Study," Circ Heart Fail., 2012, pp. 710-719, vol. 5, No. 6.
Oghlakian et al., "Treatment of Heart Failure with Preserved Ejection Fraction: Have We Been Pursuing the Wrong Paradigm?" Mayo Clin Proc., 2011, pp. 531-539, vol. 86, No. 6.
Oliver et al., "Clinical Potential of Combined Organic Nitrate and Phosphodiesterase Type 5 Inhibitor in Treatment-Resistant Hypertension," Hypertension, 2010, pp. 62-67, vol. 56, No. 1.
Omar et al., "A comparison of organic and inorganic nitrates/nitrites," Nitric Oxide, 2012, pp. 229-240, vol. 26, No. 4.
Ormerod et al., "Short-Term Intravenous Sodium Nitrite Infusion Improves Cardiac and Pulmonary Hemodynamics in Heart Failure Patients," Circ Heart Fail., 2015, pp. 565-571, vol. 8, No. 3.
Ormerod et al., "Systemic nitrite selectively dilates veins and pulmonary vasculature, relieving diastolic ventricular interaction in advanced heart failure," Eur Heart J., 2009, p. 595, vol. 30 (Abstract Supplement).
O'Rourke et al., "Mechanical Factors in Arterial Aging—A Clinical Perspective," J Am Coll Cardiol., 2007, pp. 1-13, vol. 50, No. 1.
Oudiz, "Primary Pulmonary Hypertension," Aug. 29, 2007. Downloaded from emedicine.medscape.com/article/301450. Printed on May 16, 2016 (14 pages).
Palevsky et al., "Prostacyclin and Acetylcholine as Screening Agents for Acute Pulmonary Vasodilator Responsiveness in Primary Pulmonary Hypertension," Circulation, 1990, pp. 2018-2026, vol. 82, No. 6.
Parsley et al., "P66 Nebulized inhaled nitrite (AJR001) for pulmonary arterial hypertension: Studies to determine safety, pharmacokinetics, and maximum tolerated dose, lack of pharmacodynamics interaction with sildenafil and optimal nebulizer device," Abstracts/ Nitric Oxide, 2013, pp. S13-S48, vol. 31.
Patel et al., "The potential role of the red blood cell in nitrite-dependent regulation of blood flow," Cardiovasc Res., 2011, pp. 507-515, vol. 89, No. 3.
Pinder et al., "Nitrite directly vasodilates hypoxic vasculature via nitric oxide-dependent and -independent pathways," Br J Pharmacol., 2009, pp. 1523-1530, vol. 157, No. 8.
Rado et al., "The Role of Venous Constriction in Circulatory Disorders," Br Heart J., 1958, pp. 389-396, vol. 20, No. 3.
Sindler et al., "Nitrite supplementation reverses vascular endothelial dysfunction and large elastic artery stiffness with aging," Aging Cell., 2011, pp. 429-437, vol. 10, No. 3.
Springer et al., "Pediatric Respiratory Failure," Feb. 12, 2008. Downloaded from emedicine.medscape.com/article/908172. Printed on Mar. 20, 2009 (7 pages).
The Family Practice Notebook website, "Endotracheal Tube." Downloaded from www.fpnotebook.com/Lung/Procedure/EndtrchlTb.htm on Mar. 20, 2009 (9 pages).
Udelson, "Heart Failure with Preserved Ejection Fraction," Circulation, 2011, pp. e540-e543, vol. 124, No. 21.

Van Veldhuisen et al., "Beta-Blockade with Nebivolol in Elderly Heart Failure Patients with Impaired and Preserved Left Ventricular Ejection Fraction: Data from Seniors (Study of Effects of Nebivolol Intervention on Outcomes and Rehospitalization in Seniors with Heart Failure)," J Am Coll Cardiol., 2009, pp. 2150-2158, vol. 53, No. 23.
Vanhatalo et al., "Acute and chronic effects of dietary nitrate supplementation on blood pressure and the physiological responses to moderate-intensity and incremental exercise," Am J Physiol Regul Integr Comp Physiol., 2010, pp. R1121-R1131, vol. 299, No. 4.
Vasan et al., "Prevalence, Clinical Features and Prognosis of Diastolic Heart Failure: An Epidemiologic Perspective," J Am Coll Cardiol., 1995, pp. 1565-1574, vol. 26, No. 7.
Vleeming et al., "Effect of Nitrite on Blood Pressure in Anaesthetized and Free-moving Rats," Food Chem Toxicol., 1997, pp. 615-619, vol. 35, No. 6.
Yaginuma et al., "Effect of glyceryl trinitrate on peripheral arteries alters left ventricular hydraulic load in man," Cardiovasc Res., 1986, pp. 153-160, vol. 20, No. 2.
Yamamoto et al., "Effects of carvedilol on heart failure with preserved ejection fraction: the Japanese Diastolic Heart Failure Study (J-DHF)," Eur J Heart Fail., 2013, pp. 110-118, vol. 15, No. 1.
Yusuf et al., "Effects of candesartan in patients with chronic heart failure and preserved left-ventricular ejection fraction: the CHARM-Preserved Trial," Lancet, 2003, pp. 777-781, vol. 362, No. 9386.
Zelis et al., "A Comparison of the Effects of Vasodilator Stimuli on Peripheral Resistance Vessels in Normal Subjects and in Patients with Congestive Heart Failure," J Clin Invest., 1968, pp. 960-970, vol. 47, No. 4.
Zile et al., "Diastolic Heart Failure—Abnormalities in Active Relaxation and Passive Stiffness of the Left Ventricle," N Engl J Med., 2004, pp. 1953-1959, vol. 350, No. 19.
Zuckerbraun et al., "Nitrite in pulmonary arterial hypertension: therapeutic avenues in the setting of dysregulated arginine/nitric oxide synthase signaling," Cardiovascular Research, 2011, pp. 542-552, vol. 89.
Ahmed et al., "Effects of Digoxin on Morbidity and Mortality in Diastolic Heart Failure: The Ancillary DiQuitalis Investigation Group Trial," Circulation, 2006, pp. 397-403, vol. 114, No. 5.
American Thoracic Society and American College of Chest Physicians, "ATS/ACCP Statement on Cardiopulmonary Exercise Testing," Am J Respir Grit Care Med., 2003, pp. 211-277, vol. 167, No. 2.
Anesthesia Equipment Resources: Non-Rebreathing Circuits. Downloaded from www.asevet.com/resources/circuits/nrb.hlm on Mar. 20, 2009 (2 pages).
Anonymous, "Dietary Nitrates for Heart Failure (HF)—Full Text View," ClinicalTrials.gov, 2012, pp. 1-10.
Argenziano et al., "Randomized, Double-Blind Trial of Inhaled Nitric Oxide in LVAD Recipients with Pulmonary Hypertension," Ann Thorac Surg., 1998, pp. 340-345, vol. 65, No. 2.
Bahra et al., "Inorganic nitrate ingestion improves vascular compliance but does not alter flow-mediated dilatation in healthy volunteers," Nitric Oxide, 2012, pp. 197-202, vol. 26, No. 4.
Bailey et al, "Dietary nitrate supplementation enhances muscle contractile efficiency during knee-extensor exercise in humans," J Appl Physiol., 1985, pp. 135-148, vol. 109, No. 1.
Bailey et al., "Dietary nitrate supplementation reduces the O2 cost of low-intensity exercise and enhances tolerance to high-intensity exercise in humans," J Appl Physiol., 1985, pp. 1144-1155, vol. 107, No. 4.
Baraldi et al., "Chronic Lung Disease After Premature Birth," N Engl J Med., 2007, pp. 1946-1955, vol. 357, No. 19.
Bhella et al., "Abnormal haemodynamic response to exercise in heart failure with preserved ejection fraction," Eur J Heart Fail., 2011, pp. 1296-1304, vol. 12.
Bhuiyan et al., "Heart Failure with Preserved Ejection Fraction: Persistent Diagnosis, Therapeutic Enigma," Curr Cardiovasc Risk Rep., 2011, pp. 440-449, vol. 5.

(56) References Cited

OTHER PUBLICATIONS

Bhusan et al., "Nitrite Therapy Improves Left Ventricular Function During Heart Failure via Restoration of Nitric Oxide-Mediated Cytoprotective Signaling," Circ Res., 2014, pp. 1281-1291, vol. 114, No. 8.

Bhushan et al., "Sodium Nitrite Improves Left Ventricular Function During Heart Failure via Cytoprotective Signaling and Angiogenesis," Circulation, 2018, pp. 1-5, vol. 128, No. 22.

Blood et al., "Inhaled Nitrite Reverses Hemolysis-Induced Pulmonary Vasoconstriction in Newborn Lambs Without Blood Participation," Circulation, 2011, pp. 605-612, vol. 123, No. 6.

Boilson et al., "Caveat medicus! Pulmonary hypertension in the elderly: a word of caution," Eur J Heart Fail., 2010, pp. 89-93, vol. 12, No. 1.

Borlaug et al., "Diastolic and Systolic Heart Failure Are Distinct Phenotypes Within the Heart Failure Spectrum," Circulation, 2011, pp. 2006-2014, vol. 123, No. 18.

Borlaug et al., "Global Cardiovascular Reserve Dysfunction in Heart Failure With Preserved Ejection Fraction," J Am Coll Cardiol., 2010, pp. 2138-2147, vol. 56, No. 11.

Calvert et al., "Myocardial protection by nitrite," Cardiovasc Res., 2009, pp. 195-203, vol. 83, No. 2.

Chirinos et al., "Left Ventricular Mass, Allometric Scaling, Normative Values, Effect of Obesity, and Prognostic Performance," Hypertension, 2010, pp. 91-98, vol. 56, No. 1.

Clark et al., "Low-Dose Nitric Oxide Therapy for Persistent Pulmonary Hypertension of the Newborn," N Engl J Med., 2000, pp. 469-474, vol. 342, No. 7.

Cleland et al., "The perindopril in elderly people with chronic heart failure (PEP-CHF) study," Eur Heart J., 2006, pp. 2338-2345, vol. 19.

Conraads et al., "Effects of the long-term administration of nebivolol on the clinical symptoms, exercise capacity, and left ventricular function of patients with diastolic dysfunction; results of the ELANDD study," Eur J Heart Fail., 2012, pp. 219-225, vol. 14, No. 2.

Final Office Action issued in U.S. Appl. No. 14/765,583 dated Mar. 22, 2016.

International Search Report issued in International Application No. PCT/US2014/015300 dated May 14, 2014.

International Search Report issued in International Application No. PCT/US2014/019703 dated Jun. 6, 2014.

Non Final Office Action issued in U.S. Appl. No. 14/765,583 dated Oct. 22, 2015.

Withdrawal of Appeal and Ex Parte Reexamination Communication Transmittal Form issued in U.S. Appl. No. 90/008,894 dated Mar. 18, 2010.

Crandall et al., "Acquired Tolerance to and Cross Tolerance Between the Nitrous and Nitric Acid Esters and Sodium Nitrite in Man," J Pharmacol Exp Therapeut., 1930, pp. 103-119.

Demoncheaux et al., "Circulating nitrite anions are a directly acting vasodilator and are donors for nitric oxide," Clin Sci (Lond)., 2002, pp. 77-83, vol. 102, No. 1.

Digitalis Investigation Group, "The Effect of Digoxin on Mortality and Morbidity in Patients with Heart Failure," N Engl J Med., 1997, pp. 525-533, vol. 336, No. 8.

Egemnazarov et al., "Nebulization of the acidified sodium nitrite formulation attenuates acute hypoxic pulmonary vasoconstriction," Respir Res., 2010, pp. 81-93, vol. 11.

Elias, "The Smoothie That Lowers Blood Pressure," Prevention, Apr. 19, 2013, retrieved online at: https://www.prevention.com/food-nutrition/healthy-eating/a20445586/lower-your-blood-pressure-with-beet-root-juice/.

Elkayam et al., "Effects of Nitrates and Hydralazine in Heart Failure: Clinical Evidence Before the African American Heart Failure Trial," Am J Cardiol., 2005, pp. 37i-43i, vol. 96, No. 7B.

Elkayam et al., "The Role of Organic Nitrates in the Treatment of Heart Failure," Prog Cardiovasc Dis., 1999, pp. 255-264, vol. 41, No. 4.

Ennezat et al., "Left Ventricular Abnormal Response During Dynamic Exercise in Patients with Heart Failure and Preserved Left Ventricular Ejection Fraction at Rest," J Card Fail., 2008, pp. 475-480, vol. 14, No. 6.

Ferguson et al., "Impact of dietary nitrate supplementation via beetroot juice on exercising muscle vascular control in rats," J Physiol., 2013, pp. 547-557, vol. 591, No. 2.

From et al., "Heart Failure with Preserved Ejection Fraction: Pathophysiology and Emerging Therapies," Cardiovascular Therapeutics, 2011, pp. e6-e21, vol. 29.

Fullerton et al., "Variable Response to Inhaled Nitric Oxide After Cardiac Surgery," Ann Thorac Surg., 1997, pp. 1251-1256, vol. 63, No. 5.

Gilchrist et al., "Inorganic nitrate and nitrite and control of blood pressure," Cardiovasc Res., 2011, pp. 492-498, vol. 89, No. 3.

Greig et al., "Comparative effects of glyceryl trinitrate and amyl nitrite on pulse wave reflection and augmentation index," Br J Clin Pharmacol., 2005, pp. 265-270, vol. 59, No. 3.

Hackman et al., "Phannacotherapy for Idiopathic Pulmonary Arterial Hypertension During the Past 25 Years," Pharmacotherapy, 2006, pp. 68-94, vol. 26, No. 1.

Hamdani et al., "Distinct myocardial effects of beta-blocker therapy in heart failure with normal and reduced left ventricular ejection fraction," Eur Heart J., 2009, pp. 1863-1872, vol. 15.

Hassoun, "Therapies for scleroderma-related pulmonary arterial hypertension," Expert Rev Respir Med., 2009, pp. 187-196, vol. 3, No. 2.

Haykowsky et al., "Effect of Endurance Training on the Determinants of Peak Exercise Oxygen Consumption in Elderly Patients with Stable Compensated Heart Failure and Preserved Ejection Fraction," J Am Coll Cardiol., 2012, pp. 120-128, vol. 60, No. 2.

Hoekstra et al., "Quality of life is impaired similarly in heart failure patients with preserved and reduced ejection fraction," Eur J Heart Fail., 2011, pp. 1013-1018, vol. 13, No. 9.

Holubarsch et al., "Nitrates in combination therapy: From angina to myocardial infarction and heart failure," Schwarz Pharma AG, 2003, 108 pages.

Hundley et al., "Cardiac Cycle-Dependent Changes in Aortic Area and Distensibility Are Reduced in Older Patients With Isolated Diastolic Heart Failure and Correlate With Exercise Intolerance," J Am Coll Cardiol., 2001, pp. 796-802, vol. 38, No. 3.

Ingram et al., "Low-dose sodium nitrite vasodilates hypoxic human pulmonary vasculature by a means that is not dependent on a simultaneous elevation in plasma nitrite," Am J Physiol Heart Circ Physiol., 2010, pp. H331-H339, vol. 298, No. 2.

Kapil et al., "Inorganic Nitrate Supplementation Lowers Blood Pressure in Humans: Role for Nitrite-Derived NO," Hypertension, 2010, pp. 274-281, vol. 56, No. 2.

Kelly et al., "Nitroglycerin has more favourable effects on left ventricular afterload than apparent from measurement of pressure in a peripheral artery," Eur Heart J., 199-, pp. 138-144, vol. 11, No. 2.

INORGANIC NITRITE TO IMPROVE CARDIOPULMONARY HEMODYNAMICS

CROSS-REFERENCE TO RELATED APPLICATIONS

This application is a continuation of U.S. patent application Ser. No. 15/954,304, filed Apr. 16, 2018, which is a continuation of U.S. patent application Ser. No. 14/768,198, filed on Aug. 14, 2015, which claims the benefit of priority to PCT Application No. PCT/US2014/019703, filed on Feb. 28, 2014, which claims the benefit of priority to U.S. Provisional Patent Application No. 61/771,063, filed Feb. 28, 2013. Where permitted, these applications are incorporated herein by reference in their entireties.

GOVERNMENT SUPPORT

The invention herein was made with government support under POHIL103455 awarded by the National Institutes of Health. The government has certain rights in this invention.

FIELD OF THE INVENTION

The present invention is in the field of therapeutics. Specifically the treatment of cardiopulmonary diseases using inorganic nitrite.

BACKGROUND OF THE DISCLOSURE

Sodium nitrite is a naturally occurring compound that is commonly used as a preservative in meats. Due to its vasodilative properties and involvement in the nitric oxide pathway, drug development companies and researchers are also investigating sodium nitrite as a therapeutic agent. Clinical studies using inorganic nitrite are being conducted to determine the efficacy and safety of inorganic nitrite in the treatment of pulmonary arterial hypertension, acute myocardial infarction, in transplant patients to prevent graft dysfunction, as a topical agent for chronic leg ulcers, in sickle cell disease, prevention of cerebral vasospasm, peripheral arterial disease, as an agent for cardio-protection during coronary artery bypass surgery, for use in resuscitated cardiac arrest patients, and treatment of metabolic syndrome and hypertension. Preclinical studies also indicate that sodium nitrite may be useful as an agent to kill bacteria, including bacteria associated with infections in humans.

Heart failure (HF) is major health problem in the United States (U.S.) and elsewhere. In the U.S., HF affects over 5 million people with approximately half a million new cases occurring each year. HF is the leading cause of hospitalizations in people over 65 years in age. HF has many potential causes and diverse clinical features. Symptoms of heart, failure can include dyspnea during activity or at rest, cough with white sputum, rapid weight gain, swelling in ankles, legs and abdomen, dizziness, fatigue and weakness, rapid or irregular heartbeats, nausea, palpitations, and chest pains.

Two clinical subsets of HF are diastolic heart failure (DHF) and systolic heart failure (SHF). SHF, which is also known as heart failure with reduced ejection fraction (HFrEF) involves an abnormality of the heart resulting in failure of the heart to pump blood at a rate needed for metabolizing tissues at rest and/or during exertion. DHF (also known as heart failure with preserved ejection fraction (HFpEF) is a clinical syndrome with symptoms and signs of HF, a preserved ejection fraction and abnormal diastolic function. The clinical manifestations of HFrEF and HFpEF have distinct differences in risk factors, patient characteristics, and pathophysiology. Moreover, medications proven effective in HFrEF have not been found to be effective in HFpEF. At present there are no approved treatments for HFpEF.

Although inorganic nitrite is thought to act through generation of nitric oxide (NO), its mode of action appears to differ from nitric oxide. For example, Ingram et al. (Am J. Phsiol. 298:H331-H339 (2010)) disclose that sodium nitrite causes arterial and pulmonary vasodilation in hypoxic but not normoxic subjects, and this vasodilation was not directly associated with an elevation in plasma nitrite concentration. Further, in patients with high pulmonary capillary wedge pressure (PCWP), inhaled nitric oxide can worsen the condition and cause pulmonary edema, Whereas, as disclosed herein, inhaled nitrite lowers PCWP, suggesting that it works differently than nitric oxide.

SUMMARY OF THE INVENTION

Disclosed herein are methods for treating acute or chronic heart failure by administering to a subject in need of treatment a therapeutically effective amount of inorganic nitrite. In some embodiments of this method and other methods disclosed herein the inorganic nitrite is sodium nitrite. In an aspect of this embodiment, the nitrite is administered by inhalation as a liquid or dry powder. As a liquid, the nitrite formulation may be nebulized for inhalation. In another aspect of this embodiment, the heart failure is associated with pulmonary hypertension and/or pulmonary arterial hypertension. In some aspects of this embodiment, the subject is non-responsive to inhaled nitric oxide.

In another embodiment of the methods disclosed herein, the administration of inorganic nitrite, such as inhaled inorganic nitrite, results in a decrease in one or more of right atrial pressure, pulmonary arterial pressure, pulmonary capillary wedge pressure, and pulmonary vascular resistance.

In some embodiments of the methods disclosed herein, the administration of inorganic nitrite results in improved cardiac index and/or exercise capacity.

In an another embodiment disclosed herein are methods of decreasing one or more of pulmonary capillary wedge pressure, right atrial pressure and pulmonary arterial pressure in a subject with a condition that results in one or more of increased pulmonary capillary wedge pressure, right atrial pressure and pulmonary atrial pressure by administering a therapeutically effective dose of inorganic nitrite. In an additional embodiment of this method and other methods disclosed herein, the administration of inorganic nitrite is not accompanied by a significant drop in blood pressure and increase in heart rate after administration of the inorganic nitrite. In an aspect of this embodiment, the nitrite is administered by inhalation as a dry powder or liquid. In some aspects of this embodiment, the liquid formulation is nebulized. In some aspects of this embodiment, the subject is non-responsive to inhaled nitric oxide.

Conditions that can treated using the methods disclosed herein are, without limitation, acute or chronic heart failure, including diastolic dysfunction, diastolic heart failure, or systolic heart failure, pulmonary hypertension associated with diastolic heart failure, pulmonary hypertension associated with systolic heart failure, interstitial lung disease, associated pulmonary arterial hypertension, idiopathic pulmonary arterial hypertension; and sleep-disordered breathing-related pulmonary hypertension. In some aspects of this embodiment, the subject is non-responsive to inhaled nitric oxide.

In some embodiments the associated pulmonary arterial hypertension is associated with a connective tissue disease, such as without limitation, scleroderma.

In another embodiment, disclosed herein are methods for treating a condition amenable to treatment with inorganic nitrite in a subject in need of treatment by administering a therapeutically effective amount of inorganic nitrite to a subject with tolerance to organic nitrates. The conditions amenable to treatment can include, without limitation, acute or chronic heart failure, such as diastolic dysfunction, diastolic heart failure, and/or systolic heart failure. In an aspect of this embodiment are methods for treating heart failure with preserved ejection fraction (HFpEF) or heart failure with reduced ejection fraction (HFrEF) comprising administering to a subject in need of treatment a therapeutically effective amount of inorganic nitrite. In another aspect of this embodiment, the nitrite is administered by inhalation as a dry powder or liquid. In some aspects the liquid formulation is nebulized. In some aspects, the subject is non-responsive to inhaled nitric oxide.

In an embodiment of the methods disclosed herein, the amount of inorganic nitrite administered via inhalation is an emitted dose of about 90 mg or less, or about 45 mg-90 mg, or about 25 mg-80 mg nitrite, or about 25 mg-75 mg. The dose can be one or more doses. In some embodiments, the dose or doses can be an escalated dose to reach the final highest dose concentration, such as about 90 mg, or about 80 mg, or about 75 mg. In some embodiments, the inhaled inorganic nitrite can be a liquid or dry powdered formulation. The liquid formulation can be nebulized for administration.

In another embodiment of the methods disclosed herein, the inorganic nitrite is administered at a dose of nitrite that results in a plasma concentration of nitrite of about 4 micromolar to about 15 micromolar nitrite. Modes of administration can include, without limitation, enteral, sublingual, parenteral, inhalation, such as oral, nasal, topical, transdermal, and rectal.

Disclosed herein are methods of treating pulmonary hypertension (PH) and/or pulmonary arterial hypertension (PAH) in a subject in need of treatment by determining if the subject is non-responsive to inhaled nitric oxide, wherein if the subject is non-responsive to inhaled nitric oxide the subject is administered one or more doses of inorganic nitrite to treat the PH and/or PAH. In an aspect of this embodiment the nitrite is administered by inhalation as a dry powder or liquid. In some aspects of this embodiment, the liquid formulation is nebulized. In another aspect of this embodiment, the subject has associated acute of chronic heart failure, such as diastolic dysfunction, diastolic heart failure, or systolic heart failure, for example HFrEF or HFpEF.

Disclosed herein are methods for treating acute or chronic heart failure associated with PH and/or PAH comprising by determining if the subject is non-responsive to inhaled nitric oxide, wherein if the subject is non-responsive to inhaled nitric oxide, the subject is administered one or more doses of inorganic nitrite. In aspect of this embodiment the nitrite is administered by inhalation as a dry powder or liquid. In some aspects the liquid formulation is nebulized.

In embodiment disclosed herein, the subject being treated with inorganic nitrite is non-responsive to inhaled nitric oxide and has pulmonary hypertension associated with systolic heart failure, interstitial lung disease, pulmonary arterial hypertension including associated pulmonary arterial hypertension, idiopathic pulmonary arterial hypertension; and sleep-disordered breathing-related pulmonary hypertension. In some aspects, the PAH is associated with a connective tissue disease, such as, without limitation, scleroderma.

In embodiments disclosed herein, the subjects being treated with inorganic nitrite are non-responders to intravenous epoprostenol and intravenous adenosine.

The details of one or more embodiments of the invention are set forth in the accompanying drawings and the description below. Other features, objects, and advantages of the invention will be apparent from the description and drawings, and from the claims.

All publications, patents, patent applications cited herein are hereby expressly incorporated by reference for all purposes except to the extent they are inconsistent with the disclosures herein.

DETAILED DESCRIPTION OF THE EMBODIMENTS

Figure 1:
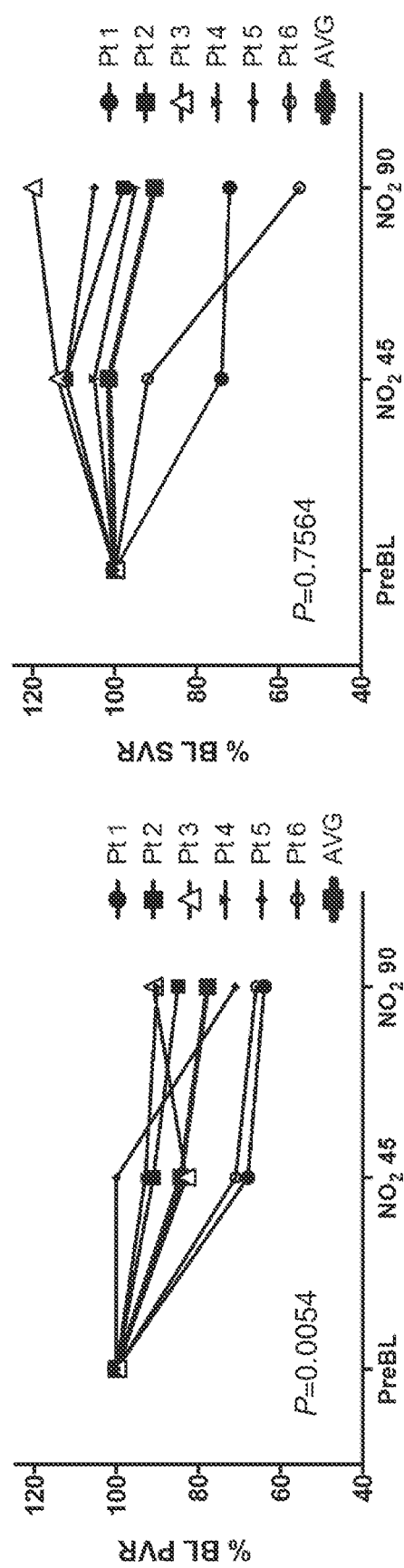
FIG. 1 shows the effect of inhaled nitrite on pulmonary vascular resistance and systemic vascular resistance in the patients described in Table 1.

Described herein are methods to treat acute or chronic heart failure in a subject in need of treatment using a therapeutically effective dose of inorganic nitrite, such as sodium nitrite.

Terms such as "treating" or "treatment" or "to treat" or "alleviating" or "to alleviate" or to "ameliorate" refer to both 1) therapeutic measures that cure, slow down, lessen symptoms of, and/or halt progression of a diagnosed pathologic condition or disorder and 2) prophylactic or preventative measures that prevent and/or slow the development of a targeted pathologic condition or disorder. Thus, those in need of treatment include those already with the disorder; those prone to have the disorder; and those in whom the disorder is to be prevented. Treatment need not result in a complete cure of the condition; partial inhibition or reduction of the condition being treated is encompassed by this term.

"Therapeutically effective amount," or "therapeutic effect," as used herein, refers to a minimal amount or concentration of inorganic nitrite that, when administered alone or in combination, is sufficient to provide a therapeutic benefit in the treatment of the condition, or to delay or minimize one or more symptoms associated with the condition. The term "therapeutically effective amount" can encompass an amount that improves overall therapy, reduces or avoids symptoms or causes of the condition, or enhances the therapeutic efficacy of another therapeutic agent.

As used herein, the term "subject" refers to an animal, typically a human (i.e., a male or female of any age group, e.g., a pediatric patient (e.g., infant, child, adolescent) or adult patient (e.g., young adult, middle-aged adult or senior adult).

In another embodiment, disclosed herein are methods for treating subjects in need of treatment who have conditions associated with high right atrial and/or pulmonary capillary wedge pressure (PCWP) using inorganic nitrite wherein the inorganic nitrite reduces one or both of either right atrial pressure or PCWP.

The term "or" is used herein to mean, and is used interchangeably with, the term "and/or", unless context clearly indicates otherwise.

Another embodiment disclosed herein are methods for treating subjects in need of treatment who have conditions associated with high pulmonary vascular resistance (PVR) using inorganic nitrite, wherein the inorganic nitrite reduces the PVR without significantly altering the systemic vascular resistance.

Disclosed herein are methods for improving cardiac index in subjects in need of treatment using inorganic nitrite, wherein the inorganic nitrite produces an improvement in cardiac index.

The methods disclosed herein are based on studies performed on subjects using the protocol described in Example 1. The subject characteristics for six subjects are given in Table 1. Raw data for each of the subjects are shown in Tables 2-7.

TABLE 1

| Subject Characteristics | | | | | | |
|---|---|---|---|---|---|---|
|  | Pt 1 | Pt 2 | Pt 3 | Pt 4 | Pt 5 | Pt 6 |
| Gender | M | M | F | F | F | F |
| Age | 59 | 65 | 48 | 69 | 60 | 69 |
| WHO category | 111 | 111 | 1 | 1 | 1 | 111 |
| WHO FC | 111 | 111b | 111b | 111b | 111 | 111 |
| Underlying disease | ILD | ILD | IPAH | IPAH | APAH SSc | ILD |
| PDE5 | — | — | sil | sil | sil | tad |
| ETRA | amb | — | amb | amb | bos | amb |
| Prostacylin | Inh tre | — | — | — | IV tre | — |

ILD is interstitial lung disease; IPAH is idiopathic pulmonary arterial hypertension; APAH is associated pulmonary arterial hypertension; SSc is systemic scleroderma; sil is sildenafil; tad is tadalafil; amb is ambrisentan; bos is bosentan; tre is treprostinil; iv is intravenous; inh is inhaled

TABLE 2

Patient 1 Characteristics

| Gender: Male | Age: 59 |
|---|---|
|  | Weight: 81.4 kg |
| WHO Category: III | WHO FC |
| Underlying | PDE5: - |
| Disease: ILD |  |
| ETRA: AMB | Prostacylin: Inh TRE |

| Date | Condition | RA | RVS | RVD | PAS | PAD | mPAP | PCWP | CO | BSA | CI | TPR |
|---|---|---|---|---|---|---|---|---|---|---|---|---|
| Jun. 15, 2012 | BL | 12 | 95 | 12 | 94 | 36 | 55.34 | 13 | 4.77 | 1.93 | 2.47 | 11.60 |
|  | iNO | 12 |  |  | 73 | 25 | 41.01 | 14 | 4.91 | 1.93 | 2.54 | 8.35 |
|  | Pre BL | 13 | 101 | 13 | 100 | 42 | 61.34 | 13 | 4.05 | 1.93 | 2.10 | 15.15 |
| nitrite 45 | 15 min | 9 | 98 | 8 | 93 | 35 | 54.34 | 11 | 4.77 | 1.93 | 2.47 | 11.39 |
|  | 30 min | 10 | 94 | 10 | 98 | 36 | 56.67 | 7 | 5.12 | 1.93 | 2.65 | 11.07 |
|  | 45 min | 9 | 95 | 9 | 100 | 38 | 58.67 | 9 | 4.85 | 1.93 | 2.51 | 12.10 |
|  | 60 min | 9 | 94 | 9 | 98 | 36 | 56.67 | 7 | 6.01 | 1.93 | 3.11 | 9.43 |
| nitrite 90 | 15 min | 3 | 96 | 3 | 92 | 32 | 52.01 | 2 | 5.65 | 1.93 | 2.93 | 9.20 |
|  | 30 min | 4 | 91 | 3 | 92 | 32 | 52.01 | 2 | 5.77 | 1.93 | 2.99 | 9.01 |
|  | 45 min | 3 | 92 | 3 | 90 | 31 | 50.67 | 2 | 6.22 | 1.93 | 3.22 | 8.15 |
|  | 60 min | 3 | 88 | 2 | 90 | 30 | 50.01 | 3 | 6.06 | 1.93 | 3.14 | 8.25 |

| Date | Condition | PVR | HR | Systemic SBP | Systemic DBP | Systemic mBP | SVR | PVR/ SVR | PA sat | Syst O2sat | metHgB |
|---|---|---|---|---|---|---|---|---|---|---|---|
| Jun. 15, 2012 | BL | 8.88 | 79 | 117 | 75 | 89.01 | 16.14 | 0.55 | 68 | 100 |  |
|  | iNO | 5.50 | 84 | 107 | 66 | 79.68 | 13.78 | 0.40 | 68 | 100 |  |
|  | Pre BL | 11.94 | 82 | 113 | 70 | 84.34 | 17.62 | 0.68 | 83 | 100 | 1.3 |
| nitrite 45 | 15 min | 9.09 | 81 | 109 | 71 | 83.68 | 15.66 | 0.58 | 66 | 95 | 1.1 |
|  | 30 min | 9.70 | 83 | 108 | 78 | 88.01 | 15.24 | 0.64 | 68 | 100 | 1.1 |
|  | 45 min | 10.24 | 82 | 109 | 72 | 84.34 | 15.53 | 0.66 | 63 | 92 | 1.3 |
|  | 60 min | 8.27 | 88 | 108 | 78 | 88.01 | 13.15 | 0.63 | 62 | 92 | 1.5 |
| nitrite 90 | 15 min | 8.85 | 93 | 97 | 67 | 77.01 | 13.10 | 0.68 | 64 | 95 | 1.4 |
|  | 30 min | 8.67 | 93 | 102 | 66 | 78.01 | 12.83 | 0.68 | 61 | 94 | 1.3 |
|  | 45 min | 7.83 | 94 | 102 | 62 | 75.34 | 11.63 | 0.67 | 62 | 94 | 1.2 |
|  | 60 min | 7.76 | 92 | 105 | 67 | 79.68 | 12.65 | 0.61 | 62 | 94 | 1.4 |

TABLE 3

Patient 2 Characteristics

| Gender: Male | Age: 65 |
|---|---|
|  | Weight: 90 kg |
| WHO Category: III | WHO FC: IIIb |
| Underlying | PDE5: - |
| Disease: ILD |  |
| ETRA: - | Prostacylin: Inh TRE |

TABLE 3-continued

| Date | Condition | RA | RVS | RVD | PAS | PAD | mPAP | PCWP | CO | BSA | CI | TPR |
|---|---|---|---|---|---|---|---|---|---|---|---|---|
| Jun. 22, 2012 | BL | 7 | 56 | 6 | 58 | 22 | 34.00 | 10 | 6.53 | 1.93 | 3.38 | 5.21 |
|  | iNO | 7 |  |  | 45 | 13 | 23.67 | 10 | 6.7 | 1.93 | 3.47 | 3.53 |
|  | Pre BL | 8 | 62 | 5 | 62 | 21 | 34.67 | 11 | 6.53 | 1.93 | 3.38 | 5.31 |
| nitrite 45 | 15 min | 6 |  |  | 57 | 19 | 31.67 | 8 | 7.08 | 1.93 | 3.67 | 4.47 |
|  | 30 min | 6 |  |  | 64 | 22 | 36.01 | 9 | 7.48 | 1.93 | 3.88 | 4.81 |
|  | 45 min | 3 |  |  | 62 | 21 | 34.67 | 8 | 7.58 | 1.93 | 3.93 | 4.57 |
|  | 60 min | 4 |  |  | 64 | 21 | 35.34 | 8 | 7.5 | 1.93 | 3.89 | 4.71 |
| nitrite 90 | 15 min | 2 |  |  | 57 | 20 | 32.34 | 8 | 7.35 | 1.93 | 3.81 | 4.40 |
|  | 30 min | 3 |  |  | 60 | 22 | 34.67 | 6 | 8.87 | 1.93 | 4.60 | 3.91 |
|  | 45 min | 3 |  |  | 62 | 21 | 34.67 | 7 | 8.09 | 1.93 | 4.19 | 4.29 |
|  | 60 min | 5 | 62 | 3 | 68 | 22 | 37.34 | 6 | 8.8 | 1.93 | 4.56 | 4.24 |

| Date | Condition | PVR | HR | Systemic SBP | Systemic DBP | Systemic mBP | SVR | PVR/SVR | PA sat | Syst O2sat | metHgB |
|---|---|---|---|---|---|---|---|---|---|---|---|
| Jun. 22, 2012 | BL | 3.68 | 76 | 139 | 80 | 99.68 | 14.19 | 0.26 | 70 | 100 |  |
|  | iNO | 2.04 | 71 | 124 | 69 | 87.34 | 11.99 | 0.17 | 68 | 100 |  |
|  | Pre BL | 3.63 | 75 | 139 | 80 | 99.68 | 14.04 | 0.26 | 83 | 100 | 1 |
| nitrite 45 | 15 min | 3.34 | 74 | 136 | 82 | 100.01 | 13.28 | 0.25 |  | 98 | 1 |
|  | 30 min | 3.61 | 73 | 137 | 75 | 95.68 | 11.99 | 0.30 |  | 99 | 1 |
|  | 45 min | 3.52 | 75 | 137 | 75 | 95.68 | 12.23 | 0.29 |  | 99 | 1 |
|  | 60 min | 3.65 | 77 | 132 | 68 | 89.34 | 11.38 | 0.32 |  | 99 | 1 |
| nitrite 90 | 15 min | 3.31 | 74 | 142 | 76 | 98.01 | 13.06 | 0.25 |  | 96 | 1.4 |
|  | 30 min | 3.23 | 74 | 132 | 77 | 95.34 | 10.41 | 0.31 |  | 98 | 1.7 |
|  | 45 min | 3.42 | 76 | 141 | 81 | 101.01 | 12.12 | 0.28 |  | 98 | 1.7 |
|  | 60 min | 3.56 | 77 | 143 | 78 | 99.68 | 10.76 | 0.33 |  | 100 | 1.6 |

TABLE 4

Patient 3
Characteristics

| Gender: Female | Age: 48 |
|---|---|
|  | Weight: 96.8 kg |
| WHO Category: I | WHO FC: IIIb |
| Underlying Disease: IPAH | PDE5: SIL |
| ETRA: AMB | Prostacylin: - |

| Date | Condition | RA | RVS | RVD | PAS | PAD | mPAP | PCWP | CO | BSA | CI | TPR |
|---|---|---|---|---|---|---|---|---|---|---|---|---|
| Aug. 1, 2012 | BL | 14 | 76 | 12 | 73 | 21 | 38.34 | 14 | 6.55 | 2.08 | 3.15 | 5.85 |
|  | iNO | 11 |  |  | 69 | 20 | 36.34 | 14 | 6.53 | 2.08 | 3.14 | 5.56 |
|  | sild/Pre BL | 16 |  |  | 70 | 26 | 40.67 | 14 | 5.31 | 2.08 | 2.55 | 7.66 |
| nitrite 45 | 15 min | 12 |  |  | 80 | 19 | 39.34 | 14 | 6.63 | 2.08 | 3.19 | 5.93 |
|  | 30 min | 10 |  |  | 70 | 20 | 35.67 | 15 | 6.4 | 2.08 | 3.08 | 5.73 |
|  | 45 min | 13 |  |  | 74 | 20 | 38.01 | 14 | 6.6 | 2.08 | 3.17 | 5.76 |
|  | 60 min | 13 |  |  | 70 | 20 | 36.67 | 14 | 6.39 | 2.08 | 3.07 | 5.74 |
| nitrite 90 | 15 min | 12 |  |  | 69 | 19 | 35.67 | 13 | 7.67 | 2.08 | 3.69 | 4.65 |
|  | 30 min | 10 |  |  | 73 | 17 | 35.67 | 11 | 5.01 | 2.08 | 2.41 | 7.12 |
|  | 45 min | 11 |  |  | 71 | 19 | 36.34 | 12 | 6.11 | 2.08 | 2.94 | 5.95 |
|  | 60 min | 9 | 71 | 8 | 72 | 20 | 37.34 | 14 | 6.95 | 2.08 | 3.34 | 5.37 |

| Date | Condition | PVR | HR | Systemic SBP | Systemic DBP | Systemic mBP | SVR | PVR/SVR | PA sat | Syst O2sat | metHgB |
|---|---|---|---|---|---|---|---|---|---|---|---|
| Aug. 1, 2012 | BL | 3.72 | 75 | 108 | 59 | 75.34 | 9.37 | 0.40 | 80 | 95 |  |
|  | iNO | 3.42 | 75 | 108 | 57 | 74.01 | 9.65 | 0.35 |  | 99 |  |
|  | sild/Pre BL | 5.02 | 71 | 109 | 66 | 80.34 | 12.12 | 0.41 |  | 94 | 0.7 |
| nitrite 45 | 15 min | 3.82 | 63 | 96 | 55 | 68.67 | 8.55 | 0.45 |  | 92 | 1.1 |
|  | 30 min | 3.39 | 51 | 95 | 56 | 69.01 | 9.22 | 0.37 |  | 94 | 1.3 |
|  | 45 min | 3.64 | 67 | 92 | 59 | 70.01 | 8.64 | 0.42 |  | 93 | 1.5 |
|  | 60 min | 3.55 | 63 | 106 | 52 | 70.01 | 8.92 | 0.40 |  | 94 | 1.5 |
| nitrite 90 | 15 min | 2.96 | 68 | 100 | 54 | 69.34 | 7.48 | 0.40 |  | 97 | 1.7 |
|  | 30 min | 4.92 | 71 | 102 | 58 | 72.68 | 12.51 | 0.39 |  | 95 | 1.7 |
|  | 45 min | 3.98 | 70 | 100 | 54 | 69.34 | 9.55 | 0.42 |  | 95 | 1.6 |
|  | 60 min | 3.36 | 72 | 103 | 59 | 73.68 | 9.31 | 0.36 |  | 95 | 1.5 |

TABLE 5

Patient 4
Characteristics

| Gender: Female | Age: 69 |
| --- | --- |
| | Weight: 73.6 kg |
| WHO Category: I | WHO FC: IIIb |
| Underlying | PDE5: SIL |
| Disease: IPAH | |
| ETRA: AMB | Prostacylin: - |

| Date | Condition | RA | RVS | RVD | PAS | PAD | mPAP | PCWP | CO | BSA | CI | TPR |
| --- | --- | --- | --- | --- | --- | --- | --- | --- | --- | --- | --- | --- |
| Sep. 21, 2012 | BL | 8 | 92 | 9 | 92 | 35 | 54.01 | 11 | 5.07 | 1.75 | 2.90 | 10.65 |
| | iNO | 3 | | | 63 | 21 | 35.00 | 7 | 5.21 | 1.75 | 2.98 | 6.72 |
| | sild/Pre BL | 7 | 71 | 5 | 74 | 24 | 40.67 | 12 | 5.2 | 1.75 | 2.97 | 7.82 |
| nitrite 45 | 15 min | 3 | 74 | 3 | 69 | 26 | 40.34 | 7 | 5.37 | 1.75 | 3.07 | 7.51 |
| | 30 min | 4 | 67 | 3 | 70 | 24 | 39.34 | 8 | 4.7 | 1.75 | 2.69 | 8.37 |
| | 45 min | 2 | 68 | 2 | 68 | 23 | 38.01 | 9 | 4.75 | 1.75 | 2.71 | 8.00 |
| | 60 min | 3 | 68 | 2 | 69 | 21 | 37.01 | 8 | 5.31 | 1.75 | 3.03 | 6.97 |
| nitrite 90 | 15 min | 3 | 62 | 3 | 71 | 23 | 39.01 | 8 | 5.39 | 1.75 | 3.08 | 7.24 |
| | 30 min | 4 | 70 | 3 | 70 | 22 | 38.01 | 7 | 5.3 | 1.75 | 3.03 | 7.17 |
| | 45 min | 2 | 74 | 2 | 69 | 23 | 38.34 | 7 | 5.39 | 1.75 | 3.08 | 7.11 |
| | 60 min | 2 | 70 | 3 | 67 | 21 | 36.34 | 8 | 5.3 | 1.75 | 3.03 | 6.86 |

| Date | Condition | PVR | HR | Systemic SBP | Systemic DBP | Systemic mBP | SVR | PVR/SVR | PA sat | Syst O2sat | metHgB |
| --- | --- | --- | --- | --- | --- | --- | --- | --- | --- | --- | --- |
| Sep. 21, 2012 | BL | 8.48 | 75 | 147 | 76 | 99.68 | 18.06 | 0.47 | 75 | 98 | |
| | iNO | 5.38 | 66 | 143 | 76 | 98.35 | 18.30 | 0.29 | | 100 | |
| | sild/Pre BL | 5.51 | 70 | 144 | 76 | 98.68 | 17.63 | 0.31 | | 97 | 1 |
| nitrite 45 | 15 min | 6.21 | 72 | 137 | 73 | 94.34 | 17.01 | 0.36 | | 98 | 1.3 |
| | 30 min | 6.67 | 69 | 134 | 77 | 96.01 | 19.58 | 0.34 | | 98 | 1.1 |
| | 45 min | 6.11 | 72 | 134 | 71 | 92.01 | 18.95 | 0.32 | | 99 | 1 |
| | 60 min | 5.46 | 71 | 131 | 71 | 91.01 | 16.57 | 0.33 | | 97 | 0.8 |
| nitrite 90 | 15 min | 5.75 | 61 | 120 | 64 | 82.68 | 14.78 | 0.39 | | 97 | 1.7 |
| | 30 min | 5.85 | 70 | 126 | 68 | 87.34 | 15.73 | 0.37 | | 97 | 2 |
| | 45 min | 5.81 | 63 | 121 | 63 | 82.34 | 14.91 | 0.39 | | 96 | 1.2 |
| | 60 min | 5.35 | 63 | 129 | 66 | 87.01 | 16.04 | 0.33 | | 96 | 1.2 |

TABLE 6

Patient 5
Characteristics

| Gender: Female | Age: 60 |
| --- | --- |
| | Weight: 70.5 kg |
| WHO Category: I | WHO FC: III |
| Underlying | PDE5: SIL |
| Disease: APAH, SSc | |
| ETRA: BOS | Prostacylin: IV TRE |

| Date | Condition | RA | RVS | RVD | PAS | PAD | mPAP | PCWP | CO | BSA | CI | TPR |
| --- | --- | --- | --- | --- | --- | --- | --- | --- | --- | --- | --- | --- |
| Sep. 28, 2012 | BL | 5 | 92 | 5 | 92 | 21 | 44.67 | 6 | 4.89 | 1.77 | 2.76 | 9.14 |
| | iNO | 5 | 66 | 5 | 64 | 17 | 32.67 | 14 | 5.05 | 1.77 | 2.85 | 6.47 |
| | sild/Pre BL | 3 | 65 | 3 | 73 | 17 | 35.67 | 7 | 5.16 | 1.77 | 2.92 | 6.91 |
| nitrite 45 | 15 min | 1 | 68 | 1 | 66 | 16 | 32.67 | 3 | 4.95 | 1.77 | 2.80 | 6.60 |
| | 30 min | 1 | | | 66 | 15 | 32.00 | 3 | 4.43 | 1.77 | 2.50 | 7.22 |
| | 45 min | 1 | | | 67 | 14 | 31.67 | 4 | 4.86 | 1.77 | 2.75 | 6.52 |
| | 60 min | 3 | 76 | 1 | 74 | 17 | 36.01 | 7 | 4.46 | 1.77 | 2.52 | 8.07 |
| nitrite 90 | 15 min | 1 | | | 76 | 16 | 36.01 | 2 | 4.91 | 1.77 | 2.77 | 7.33 |
| | 30 min | 1 | | | 69 | 16 | 33.67 | 3 | 4.97 | 1.77 | 2.81 | 6.78 |
| | 45 min | 1 | | | 70 | 13 | 32.01 | 3 | 5.07 | 1.77 | 2.86 | 6.31 |
| | 60 min | 1 | | | 74 | 14 | 34.01 | 3 | 5.73 | 1.77 | 3.24 | 5.93 |

| Date | Condition | PVR | HR | Systemic SBP | Systemic DBP | Systemic mBP | SVR | PVR/SVR | PA sat | Syst O2sat | metHgB |
| --- | --- | --- | --- | --- | --- | --- | --- | --- | --- | --- | --- |
| Sep. 28, 2012 | BL | 7.91 | 60 | 100 | 53 | 68.68 | 13.02 | 0.61 | 65 | 94 | |
| | iNO | 3.70 | 56 | 97 | 51 | 65.34 | 12.15 | 0.30 | | 100 | |
| | sild/Pre BL | 5.56 | 54 | 96 | 50 | 65.34 | 12.08 | 0.46 | | 96 | 0.6 |
| nitrite 45 | 15 min | 5.99 | 58 | 91 | 49 | 63.01 | 12.53 | 0.48 | | 94 | 1.1 |
| | 30 min | 6.55 | 53 | 95 | 52 | 66.34 | 14.75 | 0.44 | | 98 | 0.8 |
| | 45 min | 5.69 | 65 | 98 | 52 | 67.34 | 13.65 | 0.42 | 60 | 97 | 0.7 |
| | 60 min | 6.50 | 62 | 95 | 45 | 61.67 | 13.16 | 0.49 | | 94 | 0.8 |

TABLE 6-continued

| | | | | | | | | | | |
|---|---|---|---|---|---|---|---|---|---|---|
| nitrite 90 | 15 min | 6.93 | 59 | 100 | 53 | 68.68 | 13.778 | 0.50 | 95 | 0.9 |
| | 30 min | 6.17 | 61 | 102 | 49 | 66.68 | 13.21 | 0.47 | 97 | 0.7 |
| | 45 min | 5.72 | 65 | 94 | 47 | 62.67 | 12.16 | 0.47 | 98 | 0.7 |
| | 60 min | 5.41 | 58 | 107 | 54 | 71.68 | 12.33 | 0.44 | 97 | 0.5 |

TABLE 7

Patient 6
Characteristics

| | |
|---|---|
| Gender: Female | Age: 69 |
| | Weight: 94.5 kg |
| WHO Category: III | WHO FC: III |
| Underlying Disease: ILD | PDE5: Tadalafil |
| ETRA: Ambrisentan | Prostacylin: None |

| Date | Condition | RA | RVS | RVD | PAS | PAD | mPAP | PCWP | CO | BSA | CI | TPR |
|---|---|---|---|---|---|---|---|---|---|---|---|---|
| Jan. 1, 2013 | BL | 14 | 65 | 14 | 80 | 26 | 44.006 | 14 | 6.33 | 1.99 | 3.1809 | 6.952 |
| | iNO | 12 | 58 | 12 | 58 | 27 | 40.672 | 13 | 6.3 | 1.99 | 3.1658 | 6.4559 |
| | PDE5A-1/ Pre BL | 9 | 60 | 9 | 57 | 28 | 41.005 | 14 | 5.97 | 1.99 | 3 | 6.8686 |
| nitrite 45 | 15 min | 7 | | | 51 | 22 | 31.671 | 12 | 5.94 | 1.99 | 2.9849 | 5.3318 |
| | 30 min | 6 | | | 48 | 20 | 29.337 | 10 | 47.25 | 1.99 | 2.8769 | 5.1244 |
| | 45 min | 6 | | | 52 | 23 | 32.671 | 9 | 6.11 | 1.99 | 3.0704 | 5.3471 |
| | 60 min | 6 | | | 50 | 28 | 35.338 | 8 | 5.81 | 1.99 | 2.9196 | 6.0822 |
| nitrite 90 | 15 min | 6 | | | 52 | 24 | 33.338 | 9 | 6.68 | 1.99 | 3.3568 | 4.9907 |
| | 30 min | 6 | | | 48 | 20 | 29.337 | 6 | 7.3 | 1.99 | 3.6683 | 4.0188 |
| | 45 min | 6 | | | 52 | 24 | 33.338 | 4 | 7.38 | 1.99 | 3.7085 | 4.5173 |
| | 60 min | 8 | 47 | 8 | 55 | 28 | 37.005 | 4 | 8.64 | 1.99 | 4.3417 | 4.2829 |

| Date | Condition | PVR | HR | Systemic SBP | Systemic DBP | Systemic mBP | SVR | PVR/ SVR | PA sat | Syst O2sat | metHgB |
|---|---|---|---|---|---|---|---|---|---|---|---|
| Jan. 1, 2013 | BL | 4.7403 | 96 | 140 | 79 | 99.3453 | 13.483 | 0.3516 | 73 | 100 | |
| | iNO | 4.3924 | 100 | 147 | 77 | 100.346 | 14.023 | 0.3132 | | 100 | |
| | PDE5A-1/ Pre BL | 4.5235 | 99 | 134 | 73 | 93.3447 | 14.128 | 0.3202 | | 99 | 1 |
| nitrite 45 | 15 min | 3.3116 | 95 | 110 | 58 | 75.3426 | 11.505 | 0.2878 | | 95 | 1.1 |
| | 30 min | 3.3777 | 99 | 127 | 65 | 85.6773 | 13.917 | 0.2427 | | 99 | 1.3 |
| | 45 min | 3.8741 | 96 | 126 | 66 | 86.0106 | 13.095 | 0.2958 | | 96 | 1.3 |
| | 60 min | 4.7053 | 97 | 128 | 65 | 86.0107 | 13.771 | 0.3417 | | 96 | 1.2 |
| nitrite 90 | 15 min | 3.6434 | 93 | 112 | 59 | 76.6761 | 10.58 | 0.3444 | | 95 | 1.9 |
| | 30 min | 3.1969 | 95 | 110 | 66 | 80.6762 | 10.23 | 0.3125 | | 95 | 1.9 |
| | 45 min | 3.9753 | 90 | 114 | 60 | 78.0096 | 9.7574 | 0.4074 | | 96 | 1.7 |
| | 60 min | 3.82 | 91 | 111 | 58 | 75.676 | 7.8329 | 0.4877 | | 95 | 1.7 |

Inhaled sodium nitrite reduces pulmonary vascular resistance: FIG. 1 and Tables 2-7 show the response to inhaled nitrite in pulmonary and systemic hemodynamics in patients with pulmonary hypertension (PH) (WHO Group 1 and Group 3; n=6). During right heart catheterization, inhaled nitrite (in doses of 45 mg and 90 mg) produced a dose-dependent reduction in pulmonary vascular resistance (PVR) without significantly altering systemic vascular resistance (SVR) in most patients. Individual response in each patient (black) and the average for the group (larger squares).

Figure 2:
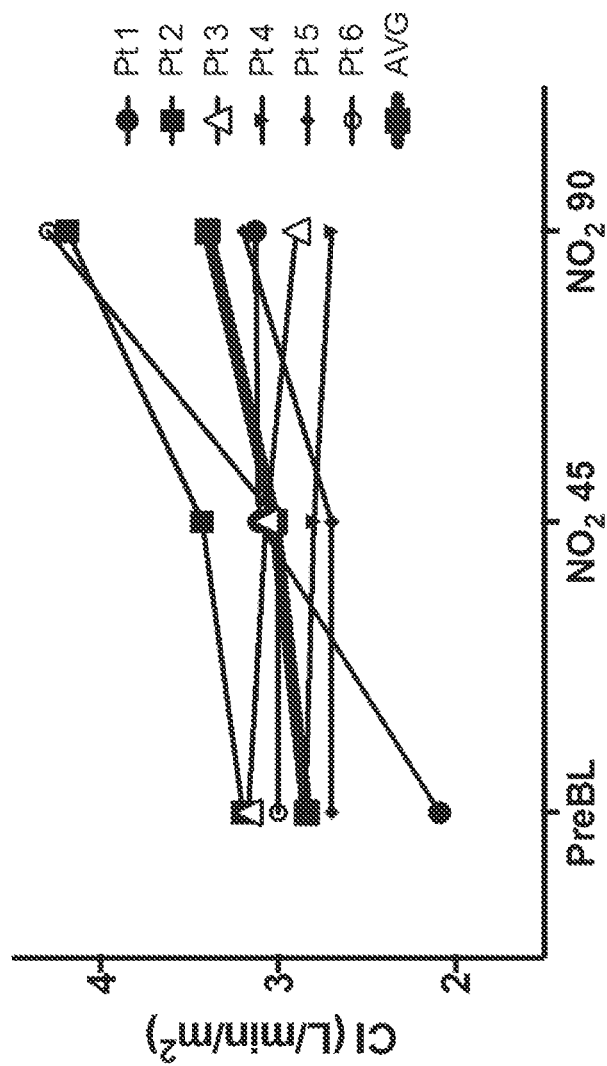
FIG. 2 shows that inhaled nitrite produced a dose-dependent improvement in cardiac index of patients described in Table 1.

Inhaled sodium nitrite improves cardiac index: FIG. 2 and Tables 2-7 show the response to inhaled nitrite in cardiac index in patients with PH (WHO Group 1 and Group 3; n=6). During right heart catheterization, inhaled nitrite (in doses of 45 mg and 90 mg placed into the nebulizer chamber) produced dose-dependent improvements in cardiac index. Individual response in each patient (black) and the average for the group (larger squares).

Figure 3:
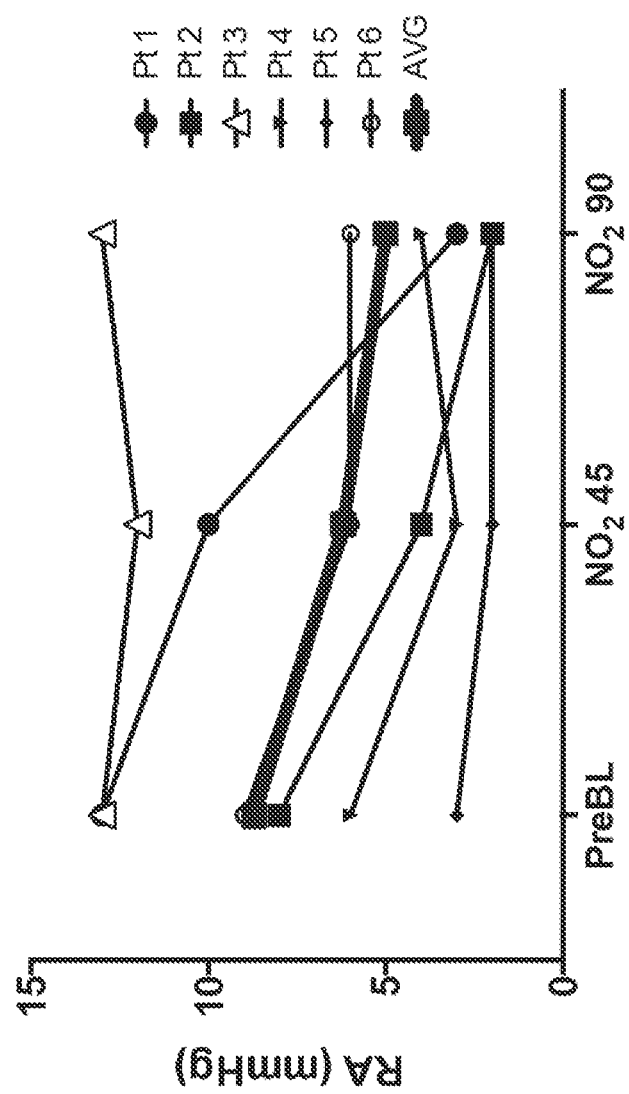
FIG. 3 shows that inhaled nitrite produced a dose-dependent reduction in right atrial pressure in the patients describe in Table 1.

Inhaled sodium nitrite reduces right atrial pressure: FIG. 3 and Tables 2-7 show the response to inhaled nitrite in RA pressure in patients with PAH (WHO Group 1 and Group 3; n=6). During right heart catheterization, inhaled nitrite (in doses of 45 mg and 90 mg placed into the nebulizer chamber) produced a dose-dependent reduction in RA pressure. Individual response in each patient (black) and the average for the group (larger squares).

Figure 4:
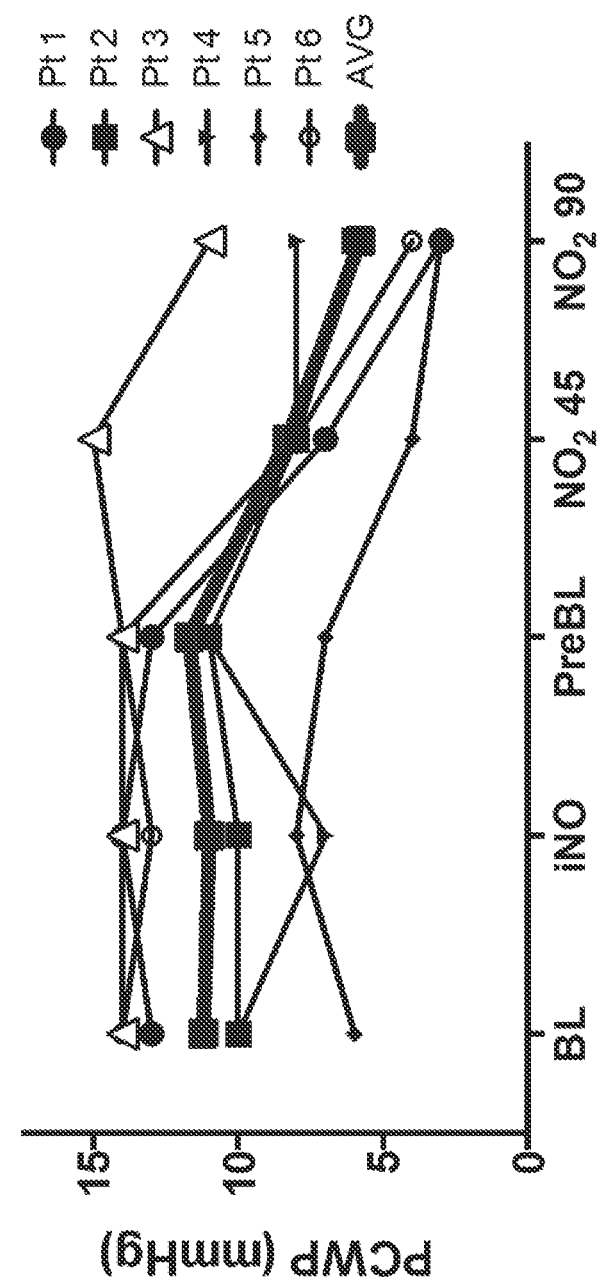
FIG. 4 shows that inhaled nitrite produced a dose-dependent reduction in pulmonary capillary wedge pressure in the patients described in Table 1.

Inhaled sodium nitrite reduces pulmonary capillary wedge pressure: FIG. 4 and Tables 2-7 show the response to inhaled nitrite in patients with PAH (WHO Group 1 and Group 3; n=6). During right heart catheterization, inhaled nitrite (in doses of 45 mg and 90 mg) produced a dose-dependent reduction in PCWP. Individual response in each patient (black) and the average for the group (larger squares).

The data disclosed in FIGS. 1-4 and Tables 2-7 indicate that inhaled inorganic nitrite would be useful for treating conditions which result in one or more of increased right atrial pressure, increased pulmonary capillary wedge pressure, increased pulmonary arterial pressure, increased pulmonary vascular resistance, decreased cardiac index, and decreased exercise capacity. Such conditions include, without limitation, acute or chronic heart failure, such as diastolic dysfunction, diastolic heart failure, systolic heart failure, pulmonary arterial hypertension associated with diastolic heart failure, pulmonary hypertension associated with systolic heart failure, interstitial lung disease, associated pulmonary arterial hypertension, idiopathic pulmonary arterial hypertension; and sleep-disordered breathing-related pulmonary hypertension. The data also indicate that at the doses tested inhaled nitrite does not significantly affect heart rate, systemic blood pressure, methemoglobin, and systemic vascular resistance.

In another embodiment, disclosed herein are methods for treating patients with inorganic nitrite who are tolerant to treatment with organic nitrates, and who have conditions that result in one or more of increased right atrial pressure, increased pulmonary capillary wedge pressure, increased pulmonary arterial pressure, increased pulmonary vascular resistance, decreased cardiac index, and decreased exercise capacity.

In conditions with decreased exercise capacity, such as heart failure, improvement in exercise capacity by inhaled inorganic nitrite can be determined using tests such as the six-minute walk where the distance walked in six minutes before treatment, by a subject in need of treatment, can be compared to the distance walked in six minutes by the subject after treatment with inorganic nitrite.

The administration of inhaled inorganic nitrite can be achieved using either a liquid formulation or a dry powder formulation. In one embodiment, the nitrite is administered via a nebulizer. In another embodiment, the nitrite is administered in a dry powder formulation, e.g., using a crushed powder delivery system. Since different devices, such as different nebulizers, deliver varying amounts of product, the doses disclosed herein are the delivered amounts, i.e., the amounts that reach the lung and are indicated as the "emitted dose". For example, the emitted dose can be about 90 mg or less of inorganic nitrite, or about 80 mg or less of nitrite, or about 70 mg or less of nitrite or about 25 mg to about 90 mg of nitrite, or about 25 mg to about 80 g of nitrite, or about 30 mg to about 90 mg nitrite, or about 40 mg to about 90 mg of nitrite, or about 45 mg to about 90 mg of sodium nitrite, or about 45 mg to about 80 mg of nitrite.

Dosing can also be done using a dose titration which escalates to the highest dose.

Figure 5:
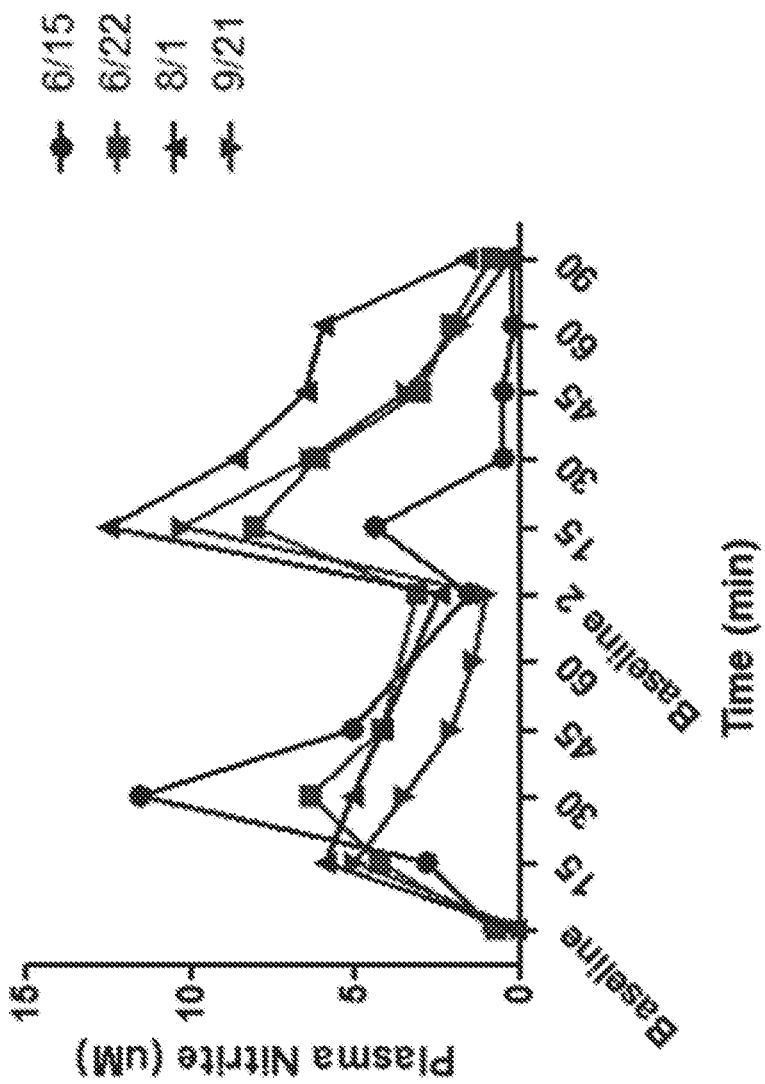
FIG. 5 shows PK data for four subjects described in Table 1 at doses of 45 mg and 90 mg inhaled sodium nitrite.

Dosing can also be based on a target plasma nitrite concentration after inhalation of nitrite. FIG. 5 shows plasma nitrite concentrations after inhalation of nitrite, and were found to be similar to normal volunteers at equivalent doses of inhaled nitrite: for the 45 mg dose 5-7 micromolar nitrite; and for the 90 mg dose 8-10 micromolar. Thus, based on these data a target plasma concentration of nitrite can be, for example, less than or equal to about 15 micromolar plasma nitrite, or less than or equal to about 12 micromolar plasma nitrite, or less than or equal to about 8 micromolar plasma nitrite, or about 5-8 micromolar plasma nitrite, or about 7-10 micromolar plasma nitrite. Generally the targeted plasma nitrite concentration will be greater than baseline and lower than 15 micromolar nitrite to about 5 micromolar plasma nitrite.

The embodiments disclosed herein will be further described with reference to the following examples; however, it is to be understood that the embodiments disclosed herein are not limited to such examples.

EXAMPLES

Example 1: Study Design

A single-center, open label phase II study evaluated the effect of inhaled nitrite delivered in a dose escalation manner on the change in pulmonary vascular resistance (PVR) in subjects with pulmonary hypertension undergoing right heart catheterization.

A total of 6 subjects with a confirmed diagnosis of pulmonary hypertension and meeting all inclusion/exclusion criteria were enrolled in the study which entailed a single right heart catheterization. The study population consisted of subjects with WHO group I PAH (n=3) and subjects with WHO group III PH (n=3) which received the dose escalation paradigm:

Each subject received a starting dose of 45 mg inhaled nitrite (nebulized nitrite), with subsequent planned dose escalation of 90 mg inhaled nitrite, based on pulmonary vascular resistance response and tolerability.

Screening (Day 0):

The potential study subjects were followed on a routine basis. Initial screening evaluations including physical examination, medical history, and clinical laboratory assessments were conducted to determine study eligibilities. Subjects who met the inclusion criteria and none of the exclusion criteria were entered into the study.

Experimental Procedures (Day 1):

The study visit occurred on the same day subjects were scheduled for their clinically indicated right heart catheterization or who volunteered for a research right heart catheterization for this specific study. WHO Group I PAH subjects on oral background PAH therapy (ETRA or PDE5A inhibitor) were instructed to take their regular regimen on the day of the study visit. If on PDE5A inhibitor the dose was timed to be 45 min before dose of nitrite.

Subjects were evaluated for additional medical history. Physical examination and baseline laboratory testing were performed to verify eligibility criteria. Baseline pulmonary artery hemodynamic assessment, echocardiogram with documentation of TRV for estimation of right ventricular systolic pressure and assessment of LV systolic and diastolic function, and micromanometry measured simultaneous pressure and flow velocity signals were performed prior to inhaled nitrite treatment. Responses to 40 ppm inhaled NO were measured before nitrite nebulization via a non-rebreather face mask to assess vasodilator responsiveness. In the study, it was found that some patients were non-responsive to inhaled NO, but were responsive to inhaled nitrite, for example, such subjects did not show a meaningful reduction in RA or PCWP from baseline. In some instances PCWP increased after inhalation of NO as compared to baseline.

Subjects received nebulized nitrite doses escalated based upon pulmonary vascular resistance response and tolerability.

The dose of inhaled nitrite was delivered via electronic nebulizer over 10 to 15 minutes. During the study right heart/pulmonary artery hemodynamics were measured as well as noninvasive systemic blood pressure monitoring and simultaneous RV echocardiography. Subjects were tested for the changes in pulmonary vascular resistance (PVR) measured by right heart catheterization and using thermodilution cardiac output measurement at time zero, at times 15, 30 and 45 minutes after completion of each nebulization dose.

Subjects were monitored closely for changes in blood pressure during the study. The presence of systemic hypotension defined by MAP ≤50 mm Hg or 20% below baseline if initial MAP <50 mm Hg would lead to a discontinuation of the study treatment, and the next higher dose of inhaled nitrite would not be administered. Subjects were continued to be monitored closely every 10 minutes for 2 hours.

Oxygen saturation measured by pulse oximeter and methemoglobin levels monitored by continuous percutaneous co-oximetry prior to dose administration and through 4 hours post-dose were monitored closely.

Blood samples were obtained after each dose of nitrite: pre-dose time zero, 15 minutes, 30 minutes, and 45 minutes; after the last dose, blood was collected at 60 and 120 minutes for nitrite PK analysis. A single blood sample was collected for Cyclic Guanosine Monophosphate (cGMP) concentration determination at the end of the peak dose of nitrite. Measurement was made on mixed venous blood using PCW pullback samples at baseline (pre-dose) and at the maximally tolerated dose.

Subjects were monitored carefully for adverse events, laboratory test abnormalities, and changes in vital signs. Adverse experiences were evaluated according to criteria outlined in the NCI Common Terminology Criteria for Adverse Events (CTCAE), version 4.0.

Following the study treatment, subjects were followed as an outpatient on Day 30. Additional follow-up assessments by telephone occurred within 24 hours of heart catheterization and on Day 3.

Study Treatment:

Following right heart catheterization, the patient was stabilized for 20 minutes. Baseline blood collections and hemodynamic measurements were performed, followed by treatment with 40 ppm inhaled NO gas for 10 minutes with repeat hemodynamic measurements performed.

After stopping inhaled NO gas, a single dose of sildenafil was given if patients were on background sildenafil therapy at previously prescribed doses. 45-minutes after sildenafil dose baseline hemodynamics were performed. Then inhaled nitrite delivered as follows.

Following completion of all baseline assessments, each subject received a starting dose of inhaled nitrite, with subsequent planned dose escalation of inhaled nitrite, based on pulmonary vascular resistance response and tolerability. Subjects were monitored carefully during and after the study treatment.

The study was conducted at the 3rd FL Catheterization Laboratory at Presbyterian Hospital of the University of Pittsburgh Medical Center (UPMC). Baseline vasoreactivity was recorded after Inhaled NO at 40 ppm for 15 minutes. Subjects received a starting dose of nebulized nitrite (45 mg), with subsequent planned dose escalation to 90 mg based upon tolerability. The dose of nebulized nitrite was delivered by an electronic nebulizer system that is portable, highly efficient utilizing continuously vibrating mesh aerosol generation technology that allows a high percentage respirable dose delivery, minimal loss of drug to the environment between inhalations, and a reproducible droplet size distribution for optimal delivery of drugs to the distal pulmonary tree over 10-15 minutes. Subjects were instructed to breathe as calmly, and deeply as possible until no more mist was formed in the nebulizer chamber. Subjects were also instructed to hold their breath for approximately 10 seconds after inhalation to allow the study drug to reach deep into the lungs.

Inclusion Criteria: WHO Group I PAH (n=20)
Diagnosis of RHC confirmed WHO Group I PAH
Idiopathic, primary or familial pulmonary arterial hypertension (IPAH, PPH, or FPAH).
PAH associated with one of the following connective tissue diseases:
  i. Systemic sclerosis (scleroderma)
  ii. Limited scleroderma
  iii. Mixed connective tissue disease
  iv. Systemic lupus erythematosus
  v. Overlap syndrome;
PAH associated with exposure to drugs and toxins (eg., anorexigens, L-tryptophan, toxic rapeseed oil)
If on current treatment with approved PDE5-I and/or ETRA, the dose is at package-insert recommended dosages as monotherapy or in combination with any continuously administered subcutaneous or intravenous prostacyclin analog
Stable PAH for at least 3 months if on therapy
WHO Group III PH (n=10)
Has WHO functional class III-IV symptoms
Had the diagnosis of PH confirmed by a cardiac catheterization with the following values:
  Mean pulmonary artery pressure (mPAP) ≥25 mm Hg (at rest)
  Pulmonary capillary wedge pressure (PCWP) or left ventricular-end diastolic pressure ≤15 mm Hg (if diagnosed with PAH)
  Pulmonary vascular resistance (PVR) ≥3 mm Hg/L/min or 2: 240 dynes*sec/cm5
Both WHO Group I PAH and WHO Group III PH
Age 18-75
Able to participate in right heart catheterization
Evidence of a personally signed and dated informed consent document indicating that the subject (or a legally acceptable representative) has been informed of all pertinent aspects of the study
Subjects who are willing and able to comply with scheduled visits, treatment plan, laboratory tests, and other study procedures Exclusion Criteria:

Age less than 18 years or greater than 75 years.
Baseline systemic hypotension, defined as MAP less than 50 mmHg;
Required intravenous inotropes within 30 days prior to study participation;
Has uncontrolled systemic hypertension as evidenced by sitting systolic blood pressure >160 mm Hg or sitting diastolic blood pressure >100 mm Hg at screening;
Has a history of portal hypertension or chronic liver disease, including hepatitis B and/or hepatitis C (with evidence of recent infection and/or active virus replication) defined as moderate to severe hepatic impairment (Child-Pugh Class B-C);
Has chronic renal insufficiency as defined by serum creatinine >2.5 mg/dL at screening or requires dialysis support;
Has a hemoglobin concentration <9 g/dL at Screening;
History of atrial septostomy;
Repaired or unrepaired congenital heart disease (CHD);
Pericardial constriction;
Restrictive or congestive cardiomyopathy;
Left ventricular ejection fraction 40% by multiple gated acquisition scan (MUGA), angiography or echocardiography;
Symptomatic coronary disease with demonstrable ischemia;
Other severe acute or chronic medical or laboratory abnormality that may increase the risk associated with study participation or investigational product administration or may interfere with the interpretation of study results and, in the judgment of the investigator, would make the subject inappropriate for entry into this study;

Has a psychiatric, addictive or other disorder that compromises the ability to give informed consent for participating in this study. This includes subjects with a recent history of abusing alcohol or illicit drugs 30 days prior to study screening Day 1 and for the duration of the study;

Poorly controlled asthma defined by active wheezing and/or cough with FEV1<70% predicted, responsive to inhaled BD (>15% increase in FEV1 with BD);

Investigators, study staff or their immediate families;

Clinically significant intercurrent illness (including lower respiratory tract infection) or clinically significant surgery within 4 weeks before the administration of study drug;

Personal or family history of congenital or acquired methemoglobinemia;

Personal history of RBC CYP B5 reductase deficiency;

Known or suspected hypersensitivity or allergic reaction to sodium nitrite or saccharin;

Personal history of glucose-6-phosphate dehydrogenase (G6PD) deficiency or any contraindication to receiving methylene blue;

History of hypersensitivity or idiosyncratic reaction to drugs from multiple drug classes;

If female, is pregnant or breast feeding, or has a positive urine or blood pregnancy test result predose;

Receipt of an investigational product or device, or participation in a drug research study within a period of 15 days (or 5 half lives of the drug, whichever is longer) before the first dose of study drug;

Blood loss or blood donation >550 mL within 90 days or plasma donation >500 mL within 14 days before administration of study drug;

Clinically indicated right heart catheterization <2 weeks

Study Endpoints:

Primary Endpoint:

The primary outcome measures for this study is change in pulmonary vascular resistance measured by right heart catheterization from time zero compared with peak effect 15 minutes post completion of nebulized dose of nitrite.

Secondary Endpoints:

The secondary endpoints measure:

Time to maximum PVR decrease;

Area under the curve (AUC) for change in PVR calculated from the start of inhalation and at times 15, 30, 45 and 60 minutes post nebulization.

Repeated measures ANOVA (RM-ANOVA) for change in PVR calculated from the start of inhalation and at times 15, 30, 45 and 60 minutes post end of nebulization.

Change in mean pulmonary artery pressure, transpulmonary gradient and cardiac output (CO)/cardiac index (CI), Change in systemic blood pressure, Change in SVR, RV systolic (dP/dtmax/IP, PWRmax/EDV, RV EF, TAPSE), RV diastolic function (dP/dtmin, Tau), Change in pulmonary vascular impedance/Wave Intensity, Change in plasma nitrite concentrations in mixed venous blood at specified time points, Change in pulmonary artery occlusion (capillary) pullback nitrite and plasma cGMP at baseline compared with peak nitrite dose.

A number of embodiments have been described herein. Nevertheless, it will be understood that various modifications may be made without departing from the spirit and scope of the embodiments disclosed. Accordingly, other embodiments are within the scope of the following claims.

What is claimed is:

1. A method of decreasing one or more of pulmonary capillary wedge pressure, right atrial pressure, and pulmonary arterial pressure in a subject, relative to the subject's capillary wedge pressure, right atrial pressure, and pulmonary arterial pressure, respectively, at the start of administration, comprising administering, by inhalation, a therapeutically effective dose of inorganic nitrite in an escalated titrated dose, wherein such administration does not cause a significant drop in systemic blood pressure and increase in heart rate.

2. The method of claim 1, wherein the subject has a condition selected from the group consisting of pulmonary hypertension associated with diastolic heart failure, pulmonary hypertension associated with systolic heart failure, interstitial lung disease, pulmonary arterial hypertension, associated pulmonary arterial hypertension, idiopathic pulmonary arterial hypertension, and sleep-disordered breathing-related pulmonary hypertension.

3. The method of claim 1, wherein the nitrite is a liquid formulation.

4. The method of claim 1, wherein the nitrite is a dry powder formulation.

5. The method of claim 1, wherein the nitrite is sodium nitrite.

6. The method of claim 1, wherein the nitrite is administered at a first dose, followed by one or more subsequent doses, greater than the first dose, that escalate to a final emitted dose at about 75 mg to about 90 mg.

7. The method of claim 1, wherein the nitrite is administered at a first dose, followed by one or more subsequent doses, greater than the first dose, that escalate to a final emitted dose at about 80 mg to about 90 mg.

8. The method of claim 1, wherein the escalated titrated dose results in a plasma concentration of nitrite of about 4 micromolar to about 15 micromolar nitrite.

9. The method of claim 1, wherein the administration of inorganic nitrite results in an improved cardiac index with respect to the cardiac index of the subject at the start of the administration.

10. The method of claim 1, wherein the administration of inorganic nitrite results in increased exercise capacity with respect to the exercise capacity of the subject at the start of the administration.

11. The method of claim 1, wherein the subject is non-responsive to inhaled nitric oxide.

12. The method of claim 1, wherein the subject has pulmonary arterial hypertension.

13. The method of claim 12, wherein the pulmonary arterial hypertension is at least partially caused by a connective tissue disease.

14. The method of claim 13, wherein the connective tissue disease is scleroderma.

15. The method of claim 1, wherein the subject has heart failure.

16. The method of claim 15, wherein the subject has heart failure with preserved ejection fraction (HFpEF) and/or heart failure with reduced ejection fraction (HFrEF).

* * * * *